US007151200B2

(12) United States Patent
Lovenberg et al.

(10) Patent No.: US 7,151,200 B2
(45) Date of Patent: Dec. 19, 2006

(54) HISTAMINE RECEPTOR H3 MODIFIED TRANSGENIC MICE

(75) Inventors: Timothy W. Lovenberg, San Diego, CA (US); Wai-Ping Leung, San Diego, CA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 713 days.

(21) Appl. No.: 09/993,159

(22) Filed: Nov. 5, 2001

(65) Prior Publication Data

US 2006/0064766 A1   Mar. 23, 2006

(51) Int. Cl.
*A01K 67/00* (2006.01)
*C12N 15/00* (2006.01)
*C12N 15/85* (2006.01)

(52) U.S. Cl. .......................... 800/18; 800/21; 435/325
(58) Field of Classification Search .................. 800/8, 800/21; 435/325
See application file for complete search history.

(56) References Cited

FOREIGN PATENT DOCUMENTS

| WO | WO 95/11894 | * | 5/1995 |
| WO | WO 95/11894 A1 | | 5/1995 |
| WO | WO 03/004637 A1 | | 1/2003 |

OTHER PUBLICATIONS

Toyota (2002, Mol. Pharmacol. vol. 62, p. 389-397.*
West, 1990, Mol. Pharmacol., vol. 38, p. 610-613.*
Perez-Garcia (Psychopharm., 1999, vol. 142, p. 215-220).*
Arrang et al. "Autoinhibition of Brain Histamine Release Mediated by a Novel Class H3 of Histamine Receptor" *Nature* (London) (1983) 302(5911):832-837.
H. Baribault and R. Kemler, "Embryonic Stem Cell Culture and Gene Targeting in Transgenic Mice", *Mol. Biol. Med.* (1989) 6(6):481-492.
Blandina et al., "Inhibition of Cortical Acetylcholine Release and Cognitive Performance by Histamine H3 Receptor Activation in Rats", *Br. J. Pharmacol.* (1996) 119(8):1656-1664.
Bradley et al., "Modifying the Mouse; Design and Desire", *Bio/Technology* (1992) 10:534-539.
Bradley et al., "Formation of Germ-line Chimaeras from Embryo-Derived Teratocarcinoma Cell Lines", *Nature* (1984) 309:255-258.
Bruns et al., "A Rapid Filtration Assay for Soluble Receptors Using Polyethylenimine-Treated Filters", *Anal. Biochem.* (1983) 132(1):74-81.
Mario R. Capecchi, "The New Mouse Genetics: Altering the Genome by Gene Targeting", *Trends in Genet.* (1989) 5(3):70-76.
Mario R. Capecchi, "Altering the Genome by Homologous Recombination", *Science* (Washington, DC) (1989) 244(4910):1288-1292.
M. J. Evans and M. H. Kaufman, "Establishment in Culture of Pluripotential Cells from Mouse Embryos", *Nature* (1981) 292(5819):154-156.

M. A. Frohman and G. R. Martin, "Cut, Paste, and Save: New Approaches to Altering Specific Genes in Mice", *Cell* (1989) 56(2):145-147.
Gantz et al., "Molecular Cloning of a Gene Encoding the Histamine H2 Receptor", *P.N.A.S. U.S.A* (1991) 88(2):429-433.
Giovannini et al., "Effects of Histamine H3 Receptor Agonists and Antagonists on Cognitive Performance and Scopolamine-Induced Amnesia", *Behav. Brain Res.* (1999) 104(1-2):147-155.
Gossler et al. "Transgenesis by Means of Blastocyst-Derived Embryonic Stem Cell Lines", *P.N.A.S.* (1985) 83:9065-9069.
Hill et al. "International Union of Pharmacology, XIII: Classification of Histamine Receptors", *Pharmacol. Rev.* (1997) 49(3):253-278.
Hooper et al., 1987, "HPRT-Deficient (Lesch-Nyhan) Mouse Embryos Derived from Germ-Line Colonization by Cultured Cells", *Nature* (1987) 326:292-295.
R. Jaenisch, "Transgenic Animals", *Science* (1988) 240(4858):1468-1474.
H. S. Kim and O. Smithies, "Recombinant Fragment Assay for Gene Targetting Based on the Polymerase Chain Reaction", *Nucleic Acids Res.* (1988) 16(18):8887-8903.
Kim et al., "Problems Encountered in Detecting a Targeted Gene by the Polymerase Chain Reaction", *Gene* (1991) 103:227-233.
Laird et al., "Structure and Expression of the Guinea-Pig α-Lactalbumin Gene", *Biochem. J.* (1988) 254:85-94.
Lin et al., "Recombination in Mouse L Cells Between DNA Introduced into Cells and Homologous Chromosomal Sequences", *P.N.A.S* (1985) 82:1391-1395.
Lin et al., "Involvement of Histaminergic Neurons in Arousal Mechanisms Demonstrated with $H_3$-Receptor Ligands in the Cat", *Brain Res.* (1990) 523:325-330.
Liu et al., "Re-Examination of [3H]Mepyramine Binding Assay for Histamine H1 Receptor Using Quinine", *Biochem. Biophys. Res. Commun.* (1992) 189(1):378-384.
Maniatis et al. *Molecular Cloning* (Cold Spring Harbor Laboratory, 1982) pp. 280-281).
Mansour et al., "Disruption of the Proto-Oncogene Int-2 in Mouse Embryo-Derived Stem Cells: A General Strategy for Targeting Mutations to Non-Selectable Genes", *Nature* (1988) 336(6197):348-352.
Molinengo et al., "Combined Action of Thioperamide Plus Scopolamine, Diphengydramine, or Methysergide on Memory in Mice", *Pharmacol. Biochem. Behav.* (1999) 63(2):221-227.
Monti et al., "Effects of Selective Activation or Blockade of the Histamine H3 Receptor on Sleep and Wakefulness", *Eur. J. Pharmacol.* (1991) 205(3):283-287.
Onodera et al., "Improvement by FUB 181, a Novel Histamine $H_3$-Receptor Antagonist, of Learning and Memory in the Elevated Plus-Maze Test in Mice", *Naunyn-Schmiedeberg's Arch. Pharmacol.* (1998) 357:508-513.

(Continued)

*Primary Examiner*—Michael C. Wilson

(57) ABSTRACT

A transgenic animal with alterations in the histamine H3 receptor gene is prepared by introduction of an altered histamine H3 receptor gene into a host animal. The resulting transgenic animals do not produce functional histamine H3 receptor molecules. Cells and cell lines derived from these animals also contain the altered histamine H3 receptor gene.

5 Claims, 2 Drawing Sheets

OTHER PUBLICATIONS

Robertson et al., "Germ-Line Transmission of Genes Introduced into Cultured Pluripotential Cells by Retroviral Vector", *Nature* (1986) 323:445-448.

E.J. Robertson, "Embryo-derived Stem Cell Lines" *Teratocarcinomas and Embryonic Stem Cells*, (E.J. Robertson, Ed., Oxford, Washington DC: IRL Press) (1987) pp. 71-112.

J. Sedivy and P. A. Sharp, "Poistive Genetic Selection for Gene Disruption in Mammalian Cells by Homologous Recombination", *P.N.A.S. USA* (1989) 86(1):227-231.

Smithies et al., "Insertion of DNA Sequences into the Human Chromosomal β-Globin Locus by Homologous Recombination", *Nature* (1985) 317(6034):230-234.

Song et al., "Accurate Modification of a Chromosomal Plasmid by Homologous Recombination in Human Cells", *P.N.A.S USA* (1987) 84:6820-6824.

K. R. Thomas and M. C. Capecchi, "Site-Directed Mutagenesis by Gene Targeting in Mouse Embryo-derived Stem Cells", *Cell* (1987) 51(3):503-512.

Thomas et al., "High Frequency Targeting of Genes to Specify Sites in the Mammalian Genome", *Cell* (1986) 44(3):419-428.

Tran et al., "Histamine H1 Receptors Identified in Mammalian Brain Membranes with [3H]Mepyramine", *P.N.A.S. USA* (1978) 75(12):6290-6294.

E. F. Wagner, "EMBO Medal Review: On Transferring Genes into Stem Cells and Mice", *EMBO J.* (1990) 9(10): 3024-3032.

West et al., "Identification of Two H3-Histamine Receptor Subtypes", *Molec. Pharmacol.* (1990) 38(5):610-613.

Wood et al., "Simple and Efficient Production of Embryonic Stem Cell-Embryo Chimeras by Coculture", *P.N.A.S. USA* (1993) 90(10):4582-4584.

Yasashita et al. (1991) "Expression Cloning of a cDNA Encoding the Bovine Histamine H1 Receptor", *P.N.A.S. USA* (1991) 88(24):11515-11519.

Dugovic, C. et al., "Altered REM Sleep, Locomotor Activity and Body Temperature in Mice", Society for Neuroscience Abstracts, vol. 27, No. 1, p. 7, Nov. 2001.

Fischer, W. et al., "Effect of Clobenpropit, A Centrally Acting Histamine H3-Receptor Antagonist, On Electroshock- And Pentylenetetrazol-Induced Seizures in Mice", Journal of Neural Trasmission, vol. 105, pp. 587-599 (1998).

Lovenberg, T.W. et al., "Cloning and Functional Expression of the Human Histamine H3 Receptor", Molecular Pharmacology, vol. 55, No. 6, pp. 1101-1107, Jun. 1999.

Lovenberg, T.W. et al., "Cloning of Rat Histamine H3 Receptor Reveals Distinct Species Pharmacological Profiles", Journal of Pharmacology and Experimental Therapeutics, vol. 293, No. 8, pp. 771-778, Jun. 2000.

Perez-Garcia, C. et al., "Effects of Histamine H3 Receptor Ligands in Experimental Models of Anxiety and Depression", Psychopharmacology, 142(2):215-20, Feb. 1999.

Takahashi et al., "Targeted Disruption of H3 Receptors Results in Changes in Brain Histamine Tone Leading to an Obese Phenotype", Journal of Clinical Investigation, vol. 110, No. 12, pp. 1791-1799 (2002).

Masaki, T. et al., "Targeted Disruption of Histamine H1-Receptor Attenuates Regulatory Effects of Leptin on Feeding, Adiposity, and UCP Family in Mice", Diabetes, vol. 50, No. 2, pp. 385-391, Feb. 2001.

Toyota et al., "Behavioral Characterization of Mice Lacking Histamine H3 Receptors", Mol. Pharmacol., vol. 61, No. 2, pp. 389-397, Aug. 2002.

Toyota, H. et al., "Characterization of Mice Lacking the Histamine H3 Receptor", Society for Neuroscience Abstracts, vol. 21, No. 1, p. 492 (Nov. 2001).

Yokoyama, H. et al., "Effect of Thioperamide, A Histamine H3 Receptor Antagonist, On Electrically Induced Convulsions in Mice", European Journal of Pharmacology, vol. 234, pp. 129-133 (1993).

* cited by examiner

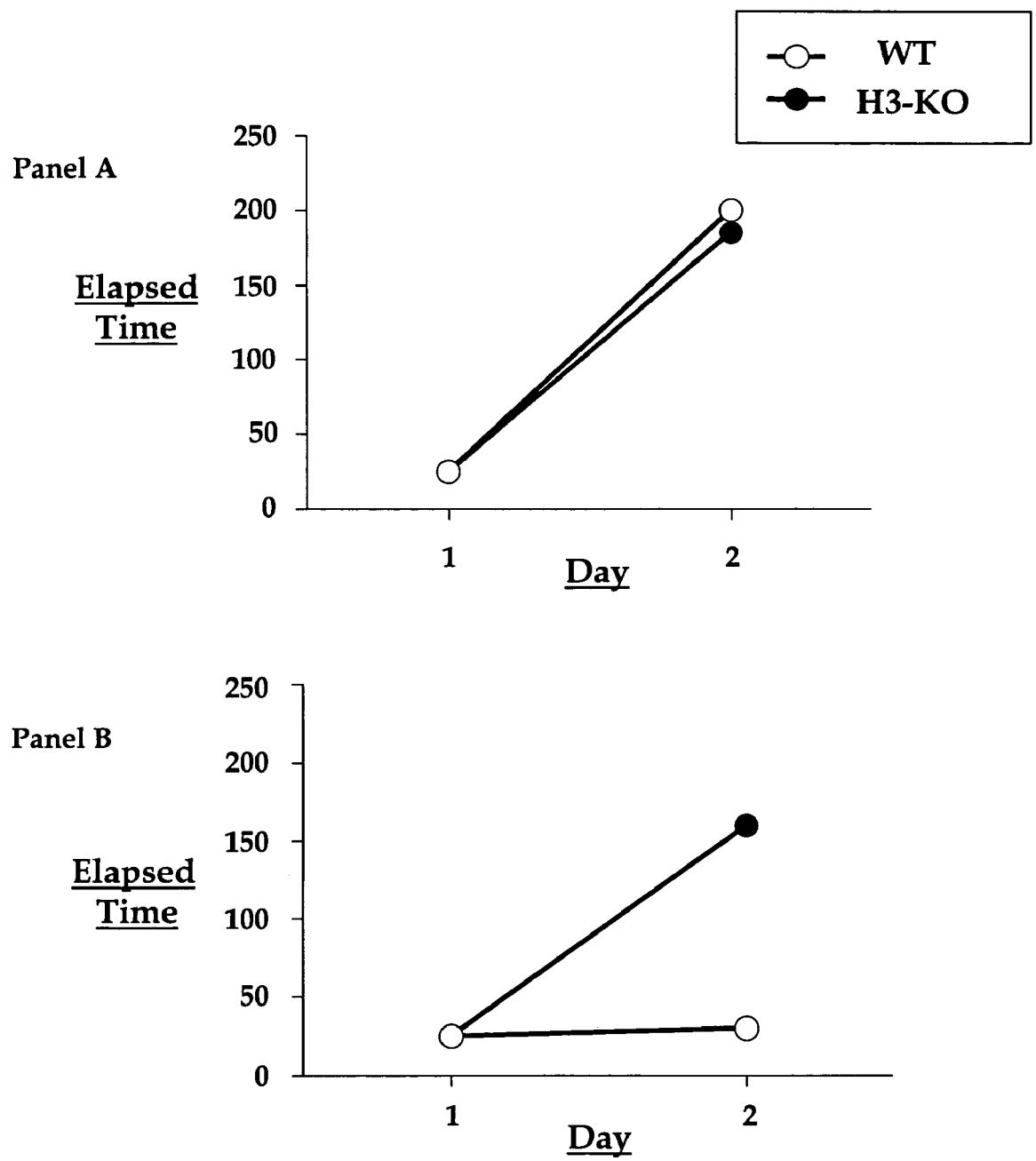

HISTAMINE RECEPTOR H3 MODIFIED TRANSGENIC MICE

FIELD OF THE INVENTION

The present invention relates to transgenic nonhuman animals wherein a histamine H3 receptor gene is altered, producing an animal lacking functional histamine H3 receptor protein.

BACKGROUND OF THE INVENTION

Histamine is a multifunctional chemical transmitter that signals through cell surface receptors that are linked to intracellular pathways via guanine nucleotide binding proteins. This class of cell surface receptors is called G-protein coupled receptors or GPCRs. There are currently three subtypes of histamine receptors that have been defined pharmacologically and have been divided into H1, H2, and H3 classifications (Hill et al. "International Union of Pharmacology, XIII, Classification of Histamine Receptors", *Pharmacol. Rev.* (1997) 49(3):253–278). The H1 histamine receptor has been cloned (Yamashita et al. (1991) "Expression Cloning of a cDNA Encoding the Bovine Histamine H1 Receptor", *P.N.A.S.*, (1991) 88(24):11515–19) and is the target of drugs such as diphenhydramine to block the effects of histamine in allergic responses. The H2 histamine receptor has been cloned (Gantz et al. "Molecular Cloning of a Gene Encoding the Histamine H2 Receptor", *P.N.A.S.* (1991) 88(2):429–33) and is the target of drugs such as ranitidine to block the effects of histamine on acid secretion in the stomach. The third subtype of histamine receptor was hypothesized to exist in 1983 (Arrang et al. "Autoinhibition of Brain Histamine Release Mediated by a Novel Class H3 of Histamine 25, Receptor", *Nature* (London) (1983) 302 (5911):832–7). It is believed to function as a pre-synaptic auto-receptor in histamine containing neurons in the central nervous system and as a pre-synaptic hetero-receptor in non-histamine containing neurons. One of the functions of the H3 receptor is to regulate neurotransmitter release at the pre-synaptic site. Histamine H3 receptors are thus expressed in the central nervous system, but have also been pharmacologically identified in heart, lung, and stomach, and have been hypothesized to exist in other tissues.

To dissect the in vivo role of histamine H3 receptor signaling pathways, a transgenic mouse was generated in the present invention in which the histamine H3 gene was disrupted by homologous recombination and histamine H3 receptor deficient fibroblasts were prepared.

SUMMARY OF THE INVENTION

To understand the functional role of histamine H3 receptor in different cell types, mice that do not express the functional histamine H3 receptor were generated by homologous recombination (HR) in embryonic stem (ES) cells and are disclosed herein. Cell lines that are derived from these mice are also disclosed herein. These mice, including the cell lines derived from them, provide a valuable animal model and tools to understand the function of histamine H3 receptor and to evaluate the therapeutic effects of drugs that modulate the function or the expression of histamine H3 receptor equivalents in human cells. The transgenic mice of the present invention exhibit insensitivity to the amnesic effects of scopolamine as compared to wild-type mice.

Figure 1:
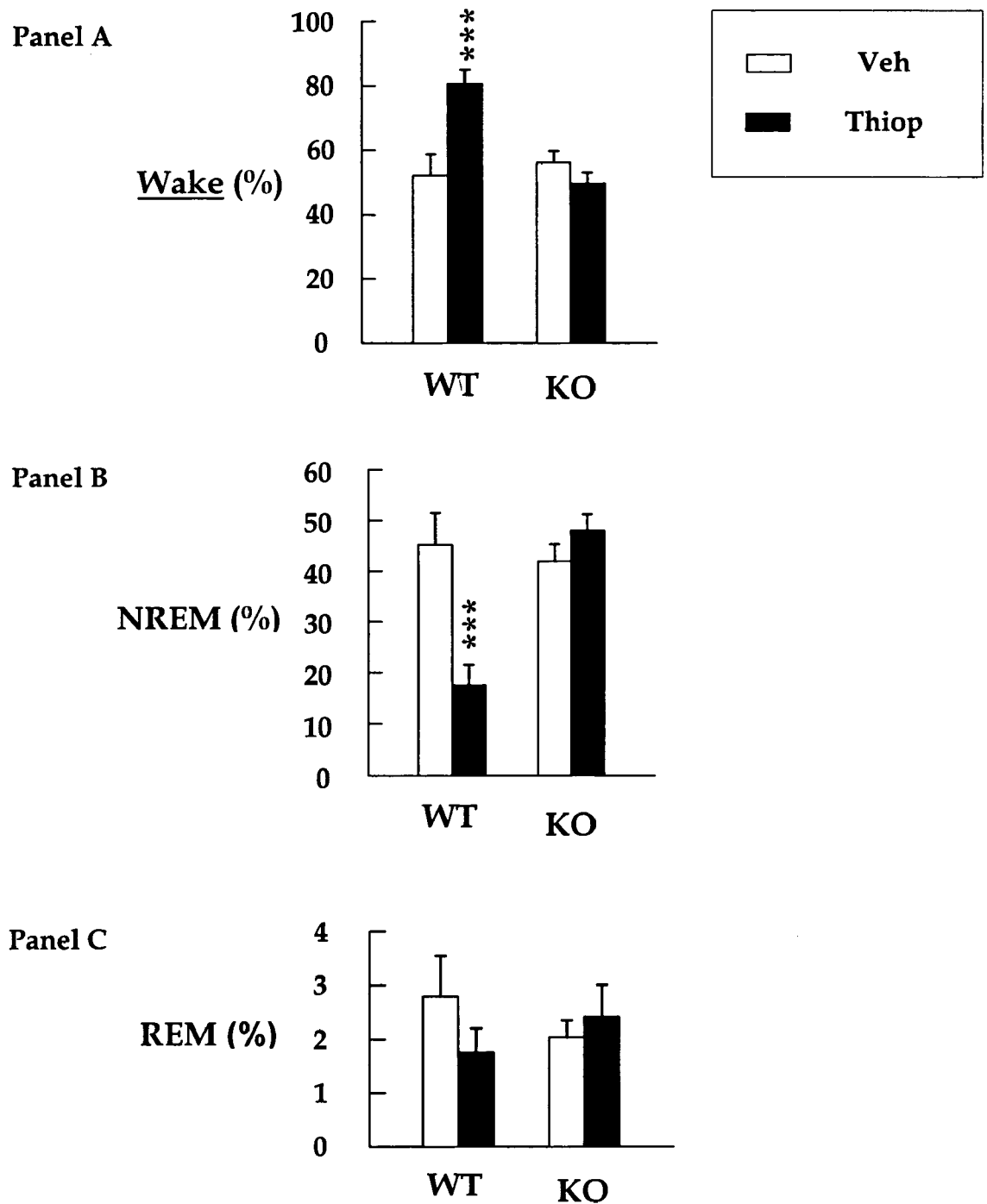
FIG. 1, Panels A, B and C.

Histamine H3 receptor knockout animals are insensitive to the H3 antagonist thioperamide. Mean (±SEM) percent time spent in each of the three vigilance states (wake, NREM and REM sleep) during the first two hours of the light period in both H3+/+ (N=6) and H3−/− (N=10) mice. The open bars represent the results in animals injected with vehicle on the baseline days, while the black bars represent the results obtained with the same animals after injection with thioperamide at the same time the next day.

\*\*\*$p<0.001$ (paired two-tailed Student t-test).

FIG. 2, Panels A and B:

H3 knockout mice exhibit decreased sensitivity to scopolamine as shown in a passive avoidance response. The left panel shows the results in untreated H3+/+ (N=29) and H3−/− (N=45) mice. Mean (±SEM) time elapsed before the mice entered the passive avoidance chamber was recorded. In the panel on the right, H3+/+ mice (N=37) and H3−/− mice (N=52) received scopolamine (0.75 mg/kg) by intra-peritoneal injection twenty minutes prior to the first test in the passive avoidance chamber. No injection was given prior to testing on the second day. (ANOVA followed by Duncan's test, * $p<0.05$)

DETAILED DESCRIPTION OF THE INVENTION

The histamine H3 receptor knockout mice that were generated in the present invention provide a model in which the histamine H3 receptor gene was disrupted by homologous recombination (HR). The process of generating the knockout mice can be divided into four basic stages:

1. cloning of the histamine H3 receptor gene and preparation of DNA construct for transfection of embryonic stem (ES) cells;
2. isolating ES cells in which the histamine H3 receptor gene has been disrupted by HR;
3. generating chimeric mice from mouse embryos injected with the knockout ES cells; and
4. breeding chimeric mice to obtain knockout mice through germ-line transmission.

The present invention utilizes a cloned genomic DNA encoding the histamine H3 receptor protein and describes the cloning and characterization of the mouse histamine H3 receptor gene. Transgenic animals are generated which have altered the histamine H3 receptor gene. The alterations to the naturally occurring gene can be modifications, deletions and substitutions. Modifications and deletions render the naturally occurring gene nonfunctional, producing a "knockout" animal. Substitution of the naturally occurring gene for a gene from a second species results in an animal that produces the gene product of the second species. Substitution of the naturally occurring gene for a gene having a mutation results in an animal that produces the mutated gene product. These transgenic animals are critical for drug antagonist or agonist studies, the creation of animal models of human diseases, and for eventual treatment of disorders or diseases associated with histamine H3 receptor-mediated responses. A transgenic animal carrying a "knockout" of histamine H3 receptor is useful for the establishment of a nonhuman model for diseases involving histamine H3 receptor equivalents in the human.

A transgenic mouse carrying the disrupted histamine H3 receptor gene was generated by homologous recombination of a target DNA construct with the endogenous gene in the chromosome. The DNA construct was prepared from a genomic clone of histamine H3 receptor that was isolated from a genomic DNA library.

The term "animal" is used herein to include all vertebrate animals, except humans. It also includes an individual animal in all stages of development, including embryonic and fetal stages. A "transgenic animal" is any animal containing one or more cells bearing genetic information altered or received, directly or indirectly, by deliberate genetic manipulation at a sub-cellular level, such as by targeted recombination or microinjection or infection with recombinant virus. The term "transgenic animal" is not intended to encompass classical cross breeding or in vitro fertilization, but rather is meant to encompass animals in which one or more cells are altered by, or receive, a recombinant DNA molecule. This recombinant DNA molecule may be specifically targeted to a defined genetic locus, may be randomly integrated within a chromosome, or it may be extra-chromosomally replicating DNA. The term "germ cell line transgenic animal" refers to a transgenic animal in which the genetic alteration or genetic information was introduced into a germ line cell, thereby conferring the ability to transfer the genetic information to offspring. If such offspring in fact possess some or all of that alteration or genetic information, they are transgenic animals as well.

The alteration or genetic information may be foreign to the species of animal to which the recipient belongs, or foreign only to the particular individual recipient, or may be genetic information already possessed by the recipient. In the last case, the altered or introduced gene may be expressed differently than the native gene, or not expressed at all.

The altered histamine H3 receptor gene generally should not fully encode the same histamine H3 receptor as native to the host animal, and its expression product should be altered to a minor or great degree, or absent altogether. However, it is conceivable that more modestly modified histamine H3 receptor genes will fall within the scope of the present invention.

The genes used for altering a target gene may be obtained by a wide variety of techniques that include, but are not limited to, isolation from genomic sources, preparation of cDNAs from isolated mRNA templates, direct synthesis, or a combination thereof.

A type of target cell for transgene introduction is the embryonal stem cell (ES). ES cells may be obtained from pre-implantation embryos cultured in vitro [M. T. Evans et al., *Nature* (1981) 292:154–156; M. O. Bradley et al., *Nature* (1984) 309:255–258; Gossler et al. *P.N.A.S.* (1985) 83:9065–9069; Robertson et al., *Nature* (1986) 322:445–448; S. A. Wood et al. *P.N.A.S.* (1993) 90:4582–4584]. Transgenes can be efficiently introduced into the ES cells by standard techniques such as DNA transfection or by retrovirus-mediated transduction. The resultant transformed ES cells can thereafter be combined with blastocysts from a non-human animal. The introduced ES cells thereafter colonize the embryo and contribute to the germ line of the resulting chimeric animal (R. Jaenisch, *Science* (1988) 240:1468–1474).

Since histamine H3 receptor is an independent component of a complex mechanism, the proteins, including that encoded by histamine H3 receptor DNA, must be examined both individually and as a group if their contribution to the mechanism is to be understood. One approach to the problem of determining the contributions of individual genes and their expression products is to use isolated genes to selectively inactivate the native wild-type gene in totipotent ES cells (such as those described herein) and then generate transgenic mice. The use of gene-targeted ES cells in the generation of gene-targeted transgenic mice was described in 1987 (Thomas et al., *Cell* (1987) 51:503–512) and is reviewed elsewhere (Frohman et al., *Cell* (1989) 56:145–147; Capecchi, *Trends in Genet*. (1989) 5:70–76; Baribault et al., *Mol. Biol. Med*. (1989) 6:481–492; Wagner, *EMBO J*. (1990) 9: 3025–3032; Bradley et al., *Bio/Technology* (1992) 10: 534–539).

Techniques are available to inactivate or alter any genetic region to any mutation desired by using targeted homologous recombination to insert specific changes into chromosomal genes. Homologous recombination was reported to be detected at a frequency between $10^{-6}$ and $10^{-3}$ (Lin et al., *P.N.A.S* (1985) 82:1391–1395; Smithies et al., *Nature* (1985) 317:230–234; Thomas et al., *Cell* (1986) 44:419–428; Song et al., *P.N.A.S* (1987) 84:6820–6824). Non-homologous plasmid-chromosome interactions are more frequent, occurring at levels $10^5$-fold (Lin et al., *P.N.A.S.* (1985) 82:1391–1395) to $10^2$-fold (Thomas et al., *Cell* (1986) 44:419–428; Song et al., *P.N.A.S* (1987) 84:6820–6824) greater than comparable homologous insertion.

To overcome this low proportion of targeted recombination in murine ES cells, various strategies have been developed to detect or select rare homologous recombinants. One approach for detecting homologous alteration events uses the polymerase chain reaction (PCR) to screen pools of transformant cells for homologous insertion, followed by screening individual clones (Kim et al., *Nucleic Acids Res*. (1988) 16:8887–8903; Kim et al., *Gene* (1991) 103:227–233). Alternatively, a positive genetic selection approach has been developed in which a marker gene is constructed which will only be active if homologous insertion occurs, allowing these recombinants to be selected directly (Sedivy et al., *P.N.A.S.* (1989) 86:227–231). One of the most powerful approaches developed for selecting homologous recombinants is the positive-negative selection (PNS) method developed for genes (such as histamine H3 receptor) for which no direct selection of the alteration exists (Mansour et al., *Nature* (1988) 336:348–352; Capecchi, *Science* (1989) 244:1288–1292; Capecchi, *Trends in Genet*. (1989) 5:70–76). The PNS method is more efficient for targeting genes that are not expressed at high levels because the marker gene has its own promoter. Non-homologous recombinants are selected against by using the Herpes Simplex virus thymidine kinase (HSV-TK) gene flanking the DNA construct. Cells with non-homologous insertion of the construct express HSV thymidine kinase and therefore are sensitive to the herpes drugs such as gancyclovir (GANC) or FIAU (1-(2-deoxy 2-fluoro-B-D-arabinofluranosyl)-5-iodouracil). By this counter-selection, the number of homologous recombinants in the surviving transformants can be increased.

As used herein, a "targeted gene" or "knockout" is a DNA sequence introduced into the germ-line of a non-human animal by way of human intervention, including but not limited to, the methods described herein. The targeted genes of the invention include DNA sequences that are designed to specifically alter cognate endogenous genes.

All the above applications have to be verified in animal tests and eventually clinical trials. One approach to determine the functional role of the drug target is to study the defects resulting from the disrupted gene in a whole animal. The histamine H3 receptor knockout mice that have been generated and are disclosed herein will allow the definition of the function of histamine H3 receptor which is critical in deciding the types of modulators are most suitable in therapies.

Any histamine H3 receptor function that is detected in the knockout mice of the present invention would provide evidence of the existence of alternative novel histamine H3 receptor subtypes that may then be isolated from the knockout mice of the present invention.

The absence of functional histamine H3 receptor in the knockout mice of the present invention are confirmed, for example, in RNA analysis, protein expression detection, receptor binding assays, enzymatic activity assays, and other histamine H3 receptor functional studies. For RNA analysis, RNA samples are prepared from different organs of the knockout mice and the histamine H3 receptor transcript are detected in Northern blots using oligonucleotide probes specific for the transcript.

Poly-serum and monoclonal antibodies that are specific for the mouse histamine H3 receptor are produced. The absence of intact histamine H3 receptor in the knockout mice is studied, for example, in flow cytometric analysis, in immunohistochemical staining, and in receptor binding and/or enzymatic activity assays using histamine H3 receptor-specific antibodies. Alternatively, functional assays are performed using preparations of different cell types collected from the knockout mice.

Mice lacking the H3 receptor gene (H3−/−) were created via homologous recombination in embryonic stem cells (129SVJ) and germ-line chimeras were crossed onto a C57B1/6J background to generate heterozygotes H3+/−. H3+/+ and H3−/− mice were created by breeding of H3+/− mice and germ-line transmission was determined by polymerase chain reaction. F2H3−/− mice were born with an expected Mendelian frequency, appeared phenotypically normal, were fertile, and appeared viable through adulthood. Growth curves for H3+/+ and H3−/− were parallel with the H3−/− animals displaying a slightly lower, but not statistically significantly different, average body weight. We verified the total absence of H3 receptors in the transgenic mice by binding studies as well as by pharmacological experiments using the selective H3 antagonist, thioperamide. While H3 receptors can be readily detected via radioligand binding in normal (H3+/+) mouse brain homogenates, H3−/− mice demonstrated a complete loss of H3 receptor binding sites as determined by $^3$H-R-α-methylhistamine binding. Heterozygote mice (H3+/−) had the same $^3$H-R-α-methylhistamine binding affinity (0.43 nM) as the H3+/+ mice (0.47 nM), but only about half the number of binding sites in whole brain homogenates (47 fmol/mg protein vs. 91 fmol/mg protein, respectively). Since it has been suggested that the H3 receptor may exist in several subtypes [R. E. West, Jr. et al., *Molec. Pharmacol.* (1990) 38:610–613], binding studies using $^3$H-R-α-methylhistamine, $^3$H-N-α-methylhistamine, or $^3$H-histamine were performed in mouse brain homogenates. No binding could be detected even at high (>100 nM) concentrations, which indicates that all H3 binding is due to a single gene product and argues against the existence of H3 receptor subtypes.

The H3 receptor is known to be involved in the regulation of sleep/waking behavior. Studies with selective H3 antagonists have shown increases in wakefulness in rats and cats [Monti et al., *Eur. J. Pharmacol.* (1991) 205:283–287; Lin et al., *Brain Res.* (1990) 523:325–330]. To confirm the absence of functional H3 receptor, we compared the effects of the H3 receptor antagonist thioperamide in WT and KO mice. This compound increased waking by 55% during the first two hours after administration at lights on in H3+/+ mice. This increase in waking was associated with a 61% decrease in non-rapid eye movement (NREM) sleep during the two-hour post injection period whereas REM sleep was not affected (FIG. 1). Importantly, there were no effects on thioperamide on the sleep-wake status of the H3−/− mice, providing behavioral confirmation that the receptor had been deleted.

The H3 receptor has also been linked to cholinergic regulation of memory and cognitive processes [Giovannini et al., *Behav. Brain Res.* (1999) 104:147–155; Blandina et al., *Br. J. Pharmacol.* (1996) 119:1656–1664]. H3 receptor antagonists have been shown to prevent scopolamine-induced amnesia in the passive avoidance. This prompted us to investigate memory in the H3−/− mouse using the step-through passive avoidance test. This test uses a light/dark preference and an acute aversive conditioning stimulus (mild foot shock) and has been used to demonstrate cognitive/memory enhancement of cholinesterase inhibitors. In a basic light/dark distribution test, there was no difference between H3+/+ and H3−/− mice either in time spent in the light or dark compartments or in the number of transitions from light to dark compartment. There was no difference between H3+/+ and H3−/− mice in the basic passive avoidance test where both sets of mice were equally able to retain the recollection of the aversive stimulus (FIG. 2B). When the H3+/+ mice were pretreated with the amnesic agent scopolamine (a muscarinic receptor antagonist) prior to their first exposure to the chamber, they failed to recall the aversive stimulus upon reintroduction to the chamber on the next day (FIG. 2B, right panel). However, the H3−/− mice were completely unresponsive to the amnesic effects of scopolamine and responded similarly as the untreated group (FIG. 2B, left panel). This is consistent with previous reports showing that thioperamide could at least partially prevent the effects of scopolamine [Giovannini et al., *Behav. Brain Res.* (1999) 104:147–155; Blandina et al., *Br. J. Pharmacol.* (1996) 119:1656–1664); Onodera et al., *Naunyn-Schmiedeberg's Arch. Pharmacol.* (1998) 357:508–513; Molinengo et al., *Pharmacol. Biochem. Behav.* (1999) 63:221–227]. These findings establish a critical role for histamine and the H3 receptor in the cholinergic pathways modulating memory function and/or cognitive processes. In addition, H3−/− mice are resistant to the amnesic effect of the cholinergic antagonist, scopolamine.

The following examples are presented for the purpose of illustrating the present invention and are not to be construed as a limitation on the scope of this invention.

EXAMPLE 1

Generation of H3−/− Animals

Mouse H3R gene clones were isolated from a 129/Ola mouse genomic library and phage clones covering 13 kb of the mouse H3R gene were isolated. The XhoI DNA fragments containing the second exon of the mouse H3R gene was used to prepare the knockout construct. A cassette containing a neomycin resistance gene was used to replace a 0.7 kb region covering part of the first intron and the 5' end of the second exon of the gene. An HSV-thymidine kinase cassette was placed at the 3' end of the construct. The mouse H3R gene, the neomycin resistance gene and the HSV-thymidine kinase gene in the construct are in the same orientation of transcription. The DNA construct was introduced into E14 embryonic stem cells by electroporation. Cells were cultured in the presence of 400 µg/ml G418 and 0.2 μM gancyclovir. Embryonic stem cells with the disrupted gene were detected by polymerase chain reaction (PCR) and then confirmed by Southern hybridization using a DNA probe flanking the 3' end of the construct. Chimeric mice were generated from embryos injected with embryonic stem cells. Germ-line mice were obtained from breeding of chimeric male mice with C57BL/6J females. Germ-line mice heterozygous for the disrupted H3R gene were identified by PCR. H3R-deficient mice carrying only the disrupted H3R gene were obtained from crossbreeding of heterozygous mice.

Transfection of ES Cells with the Histamine H3 Receptor DNA Construct

Embryonic stem (ES) cells E14 (Hooper et al., 1987, "HPRT-Deficient (Lesch-Nyhan) Mouse Embryos Derived from Germ-Line Colonization by Cultured Cells", *Nature* (1987) 326:292–295) were maintained at an undifferentiated stage by co-culturing with embryonic fibroblasts (EF) and in culture medium DMEM (15% FCS, 1 mM sodium pyruvate, 0.1 mM b-mercaptoethanol, 2 mM L-glutamine, 100 U penicillin and 100 U streptomycin) containing 1000 U/ml leukemia inhibitory factor (LIF) (Gibco). EF cells were primary fibroblast cultures prepared from Day 15 to 17 mouse fetuses according to the method described by Robertson (E. J. Robertson, "Embryo-derived Stem Cell Lines" *Teratocarcinomas and Embryonic Stem Cells*, (E. J. Robertson, Ed., Oxford, Washington D.C.: IRL Press) (1987) pp. 71–112.). EF were treated with 10 mg/ml mitomycin C (Sigma) in culture medium for two hours to stop cell division prior to the use as feeder cells.

For DNA transfection, the DNA construct was linearized by NotI digestion. DNA was then precipitated by two volumes of ice-cold ethanol at −20° C. for one hour. Precipitated DNA was pelletted by centrifugation, rinsed once with 0.5 ml 70% ethanol, air dried and then dissolved at 1 mg/ml in phosphate-buffered saline (Gibco). ES cells were harvested by trypsin treatment and re-suspended at $6.25\times10^6$ cell/ml in culture medium. DNA construct (20 μg) was added to 0.8 ml of ES cell suspension for electroporation at 250 μF and 340 Volts using the Gene Pulser (BioRad).

Transfected ES cells were plated onto EF coated 90 mm plates at $2.5\times10^6$/plate in culture medium. Two days later, cells were subjected to drug selection in medium containing 400 μg/ml G418 (Geneticin, Gibco) and 2 μM GANC (Cytosin, Syntex). Culture medium was changed daily. Massive cell death was obvious starting Day 4 and most of the dead cells were removed through daily medium change. Surviving cell colonies were observable under microscope by Day 7 and by Day 10 they were visible on the plates without a microscope.

PCR Screen of Transfected ES Cells for Homologous Recombination

The size of ES colonies on Day 11 after transfection was large enough for PCR screening. To collect cell colonies, culture medium in the 90 mm plates was aspirated and 10 ml PBS was added. Individual cell colonies were located with the aid of a stereomicroscope, collected in a 20 ml volume and transferred into 96 well plates. To prepare single cell suspension of the ES colonies, 25 μl of 0.25% trypsin (Gibco) was added per well in 96 well plates. After eight minutes of trypsin treatment at 37° C., 25 μl of culture medium was added. All the ES colonies were still maintained in culture as master plates while screening by PCR for homologous recombination events was performed. To prepare master plates, 60 μl of each cell sample was transferred to 96-well plates that had been coated with EF cells and contained 180 μl/well of the culture medium containing G418 and GANC.

For the first round PCR screen, each cell lysate sample was prepared from twelve cell colonies that arrayed as one row of samples in the 96 well plates. After the preparation of master plates, the remaining cell samples of about 90 μl/well on every row of the plates were pooled. Cells were pelletted in tubes by centrifugation for one minute. After draining the medium, cells were lysed by adding 30 μl distilled water and brief mixing. Cell lysates were prepared by first heating at 95° C. for ten minutes, cooling to room temperature and followed by an addition of 1 μl proteinase K (10 mg/ml in water) with brief mixing, a 90 minute incubation at 50° C. for proteinase K digestion, and then ten minutes at 95° C. for heat inactivation of proteinase K.

PCR was carried out using the 9600 GeneAmp system (Perkin Elmer). The reaction mixtures contained 5 μl cell lysate, 4 μM of each of the two oligonucleotide primers, 200 μM each of dATP, dTTP, dCTP, and dGTP, and 5 U AmpliTaq DNA polymerase in PCR buffer (10 mM Tris-Cl, pH8.3, 50 mM KCL, 1.5 mM $MgCL_2$ and 0.001% w/v gelatin). The reaction condition was three cycles of two minutes at 94° C., two minutes at 60° C., and two minutes at 72° C., then 40 cycles of fifteen seconds at 94° C., fifteen seconds at 60° C., and one minute at 72° C., followed by seven minutes at 72° C.

ES cells in master plates after three to four days culture were ready for splitting. Cell colonies in the positive groups were screened individually by a second round of PCR to identify the positive individual colonies. To maintain the positive groups in culture, cells in the wells were trypsinized by first removing the culture medium, rinsing once with 50 μl PBS, treating with 40 μl 0.25% trypsin for five minutes at 37° C., followed by adding 90 μl culture medium. Cells were then re-suspended and 20 μl of the cell samples were transferred to master plates that had been coated with EF and filled with 200 μl culture medium containing G418 and GANC. The remaining cells (110 μl/well) were transferred into tubes. Cell lysates were prepared and homologous recombination signals were amplified by PCR and detected by hybridization as described in the previous paragraphs.

Confirmation of Homologous Recombination by Genomic Southern Hybridization

Homologous recombination was confirmed by Southern hybridization. ES cells derived from the positive colonies in PCR screen were expanded in culture and DNA was extracted as described by Maniatis et al. *Molecular Cloning* (Cold Spring Harbor Laboratory, 1982) pp. 280–281). Genomic DNA samples of the putative knockout cell lines were digested with the restriction enzymes EcoRI, separated by 1% agarose gel electrophoresis, blotted onto Hybond-N+ nylon membranes (Amersham) and hybridized with a ~440 bp DNA fragment specific for the mouse histamine H3 receptor gene. This DNA probe did not hybridize to the DNA constructs that were integrated randomly in the chromosome.

Only the functional histamine H3 receptor was detected in the parental ES cells and only the disrupted histamine H3 receptor gene was found in knockout ES cells.

Generation of Chimeric Mice by Embryo Injection

Mouse embryos at 3.5 day gestation stage were collected from the uteri of super-ovulated C57BL/6J mice. About ten to fifteen ES cells were injected into the blastocoel cavity of the embryos. Injected embryos were transferred into the uteri of pseudo-pregnant CD1 mice at 2.5 day gestation.

Mice developed from these embryos were born seventeen days later. Since the ES cells used were derived from the 129 Ola mouse strain with the dominant agouti coat color genes, chimeric mice were identified by the agouti coat color from ES derived cells, versus the black color from C57BL/6J mouse embryos.

ES Germ-Line Mice Obtained by Chimeric Mouse Breeding

Chimeric mice were bred with C57BL/6J mice. These crosses are performed to test for the germ-line transmission of ES cells. Some of the progeny from the breeding are expected to be agouti if the chimeric male had germ line cells derived from ES cells that carry the dominant agouti coat color genes. The disrupted histamine H3 receptor gene in mice was detected by genomic hybridization as described in the previous section. Genomic DNA is purified from about 1 cm of tail from each agouti mouse after weaning. The genomic DNA is isolated as described (Laird et al., supra), followed by phenol and phenol: chloroform extractions and ethanol precipitation. Genomic DNAs are digested with EcoRI, and hybridized with the 3' flanking DNA specific for the histamine H3 receptor gene as described earlier. Since the histamine H3 receptor gene is X-chromosome linked, all the female germ-line agouti mice are heterozygous for the disrupted histamine H3 receptor gene.

Generation of Homozygous Knockout Mice from Breeding of Heterozygous Knockout Mice Female heterozygous knockout mice were mated with C57BL/6J mice or wild-type male littermates. It is expected that half of the male pups carry only the disrupted gene and half of the female pups are heterozygous for the disrupted gene. Surviving offspring were genotyped by Southern hybridization as described above. Homozygous female mice were obtained by further breeding of heterozygous females with knockout males.

EXAMPLE 2

Characterization of Histamine H3 Receptor Knockout Mice and Cells Derived from the Mice Housing and Recording of Sleep, Activity and Body Temperature Individually housed animals were maintained on a 12:12 light/dark (LD) cycle except in one study when the animals were transferred to constant darkness (DD). At three months of age, animals were implanted under deep anesthesia (ketamine 100 mg/kg and xylamine 10 mg/kg administered intraperitoneally) with EEG and EMG electrodes for sleep monitoring, and intraperitoneal biotelemetry transducers for the recording of body temperature and total locomotor activity. Two weeks after surgery and habituation to the recording chamber, body temperature and locomotor activity were monitored in baseline conditions for two consecutive days. In order to test the functional activity of H3 receptors, the effects of the H3 receptor antagonist thioperamide on sleep-wake states were examined. Mice were injected with saline one day, and thioperamide the next day. Injections occurred at the onset of the light phase and sleep EEG was recorded for the next six hours. A second group of H3+/+ and H3−/− mice were placed in running wheel cages at three months of age. Locomotor activity was recorded for three weeks under LD12:12 conditions and then the animals were transferred to constant darkness for two weeks. The results are shown in FIG. 1, panels A, B, and C.

Measurement of H3 and $H_1$ Receptor Binding and Activity

Preparation of Membrane Fraction

The mice were sacrificed by gas ($CO_2$) and decapitated immediately. Brains were removed stored at −80° C. until use. The forebrain and the cerebellum tissue homogenized with a polytron in ice-cold 50 mM Na/K phosphate buffer, pH 7.5. The homogenates were centrifuged twice at 50,000×g for twenty minutes at 4° C.

The Histamine H3 Binding Assay

The histamine H3 receptor binding was assayed by a modification of the method of Arrang et al. (1983) supra. Briefly, to examine inhibition curves, 0.4 ml aliquots of the suspensions (10 mg weight tissue) were incubated for sixty minutes at 25° C. with 1.5 nM [$^3$H]-R-alpha-MeHA. Specific binding was defined as that inhibited by 10 μM thioperamide. That reaction was terminated by addition of 5 ml of the ice-cold buffer and rapid filtration on a glass fiber filter (GF/B) pre-coated with 0.3% polyethyleneimine (Bruns et al., 1983). The filters were washed three times with 5 ml volumes of the ice-cold buffer, and the radioactivity trapped on the filters was counted in 10 ml of ScintiVerse (Fisher Scientific).

The Histamine $H_1$ Binding Assay

The histamine $H_1$ binding was assayed by a modification of the method of Tran et al. (1978). In brief, 25 μg of brain membrane was used for the ligand-binding assay with [$^3$H]pyrilamine and with 1 μM quinine to prevent binding to the P450-like protein (Liu et al., 1994) (25° C.). Concentrations of [$^3$H]pyrilamine of 0.625–10 nM were used for Scatchard analysis. Nonspecific binding was determined in the presence of 50 μM triprolidine. The samples were counted in the same way as described above.

Passive Avoidance Test

The apparatus consisted of two compartments; one (9.5× 18.5×16 cm) being surrounded by a white wall and illuminated by a 60 watt lamp, and the other (9.5×18.5×16 cm) being dark surrounded by a black wall. The compartments were separated by a guillotine door (4.5 5 4.5 cm). All the mice were habituated to the dark chamber for sixty minutes prior to the test. On the first day of the passive avoidance test, wild-type and knockout mice were divided into two groups. One group of each genotype was injected with scopolamine (0.75 mg/kg, i.p., thirty minutes before the session) while the other groups were injected with biological saline, 0.9% (w/v) NaCl, (1 mg/kg, i.p.). The mice were placed into the illuminated safe compartment for thirty seconds before being given free access to the dark box. The mice tended to escape into the dark compartment. When all four paws were on the grid floor of the dark compartment, a scrambled constant current foot shock (1 mA, constant voltage 120 V, 50 Hz) was delivered to the grid for one second. Then the mice were returned to their home cages. Twenty-four hours later, the procedure, without the electric shock, was repeated. The time that elapsed before each mouse entered the dark compartment was measured. The latency value of 300 seconds was assigned when animals did not enter the dark compartment within 300 seconds. The results are shown in FIG. 2, panels A and B.

What is claimed is:

1. A transgenic mouse whose somatic and germ cells comprise a homozygous disruption in an endogenous histamine H3 receptor gene, wherein said disruption is generated by targeted replacement with a non-functional histamine H3 receptor gene, and wherein said homozygous disruption results in said mouse having an insensitivity to amnesic effects of scopolamine as demonstrable in a passive avoidance test as compared to wild-type histamine H3 receptor mice.

2. The mouse of claim 1, wherein said mouse is fertile and transmits the non-functional histamine H3 receptor gene to its offspring.

3. A cell isolated from the transgenic mouse of claim 1.

4. A method for producing a transgenic mouse whose somatic and germ cells comprise a disruption in an endogenous histamine H3 receptor gene, wherein said disruption is generated by targeted replacement with a non-functional histamine H3 receptor gene, said method comprising:
   a) introducing a histamine H3 receptor gene targeting construct comprising a selectable marker into a mouse embryonic stem cell;
   b) introducing the embryonic stem cell into mouse blastocysts;
   c) transplanting the blastocysts into a recipient pseudopregnant mouse;
   d) allowing the blastocysts to develop to term;
   e) identifying a transgenic mouse whose genome comprises a disruption of the endogenous histamine H3 receptor gene in at least one allele; and
   f) breeding the mouse of step (e) to obtain a transgenic mouse whose genome comprises a homozygous disruption of the endogenous histamine H3 receptor gene, wherein said disruption results in said mouse having an insensitivity to amnesic effects of scopolamine as demonstrable in a passive avoidance test as compared to wild-type histamine H3 receptor mice.

5. Method of claim 4 wherein the introducing of step (a) is by electroporation or microinjection.

* * * * *

Adverse Decision in Interference

Patent No. 7,151,200, Timothy W. Lovenberg and Wai-Ping Leung, HISTAMINE RECEPTOR H3 MODIFIED TRANSGENIC MICE, Interference No. 105,663, final judgment adverse to the patentees rendered April 17, 2009, as to claims 1-3.

(*Official Gazette, January 12, 2010*)